United States Patent
Aikawa et al.

(10) Patent No.: US 10,677,452 B2
(45) Date of Patent: Jun. 9, 2020

(54) HEATING TOOL

(71) Applicant: KAO CORPORATION, Tokyo (JP)

(72) Inventors: Shohei Aikawa, Sumida-ku (JP); Youichi Endo, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 162 days.

(21) Appl. No.: 15/745,894

(22) PCT Filed: Jul. 21, 2016

(86) PCT No.: PCT/JP2016/071420
§ 371 (c)(1),
(2) Date: Jan. 18, 2018

(87) PCT Pub. No.: WO2017/014271
PCT Pub. Date: Jan. 26, 2017

(65) Prior Publication Data
US 2018/0209637 A1    Jul. 26, 2018

(30) Foreign Application Priority Data

Jul. 21, 2015 (JP) ................. 2015-144450
Jun. 29, 2016 (JP) ................. 2016-128749

(51) Int. Cl.
*A61F 7/03* (2006.01)
*F22B 3/00* (2006.01)
*F24S 30/00* (2018.01)

(52) U.S. Cl.
CPC ............ *F22B 3/00* (2013.01); *A61F 7/03* (2013.01); *F24S 30/00* (2018.05)

(58) Field of Classification Search
CPC .... F22B 1/20; F22B 3/00; F01K 3/188; A61F 7/03; A61F 7/034; F24J 1/00
See application file for complete search history.

(56) References Cited

U.S. PATENT DOCUMENTS 6,436,128 B1    8/2002  Usui
6,629,964 B1 *  10/2003 Ono .................... A61F 7/03
                                                          602/48

(Continued)

FOREIGN PATENT DOCUMENTS

JP          9-75388 A      3/1997
JP       2002-155273 A     5/2002

(Continued)

OTHER PUBLICATIONS

International Search Report dated Sep. 13, 2016 in PCT/JP2016/071420 filed Jul. 21, 2016.

(Continued)

*Primary Examiner* — Gregory A Wilson
(74) *Attorney, Agent, or Firm* — Oblon, McClelland, Maier & Neustadt, L.L.P.

(57) ABSTRACT

A heating tool (100) according to the present invention includes a steam generator (10) that a heat generating layer (11) which contains an oxidizable metal, a carbon component, a water absorbent polymer, and water, and a water absorbent sheet (102) which carries water are laminated, and a bag (20) at least a portion of which has an air permeability and accommodates the steam generator (10), in which a mass ratio of the water absorbent sheet (102) is equal to or greater than 0.9 and equal to or less than 15 with respect to the water absorbent polymer contained in the heat generating layer (11).

21 Claims, 2 Drawing Sheets

(56) References Cited

U.S. PATENT DOCUMENTS

| | | |
|---|---|---|
| 6,863,682 B2 | 3/2005 | Usui |
| 8,343,203 B2 * | 1/2013 | Ishikawa .................. A61F 7/034 607/114 |
| 9,534,810 B2 * | 1/2017 | Oka ......................... A61F 7/034 |
| 9,671,134 B2 | 6/2017 | Saita et al. |
| 9,920,954 B2 * | 3/2018 | Nishioka ................. A61F 7/034 |
| 9,945,584 B2 * | 4/2018 | Yasuda ................... A61F 7/034 |
| 2002/0151947 A1 | 10/2002 | Usui |
| 2004/0217325 A1 * | 11/2004 | Usui ........................ A61F 7/034 252/70 |
| 2007/0068508 A1 | 3/2007 | Wong |
| 2008/0234789 A1 | 9/2008 | Freeland et al. |
| 2010/0241199 A1 * | 9/2010 | Hidaka ................... A61F 7/034 607/96 |
| 2011/0190714 A1 * | 8/2011 | Oda ......................... A61F 7/03 604/291 |
| 2012/0022621 A1 | 1/2012 | Wong et al. |
| 2012/0145189 A1 * | 6/2012 | Knopow ................. A47L 13/16 134/6 |
| 2015/0320589 A1 * | 11/2015 | Nishioka ................... A61F 7/03 607/112 |

FOREIGN PATENT DOCUMENTS

| | | |
|---|---|---|
| JP | 2013-128678 A | 7/2013 |
| JP | 2013-146554 A | 8/2013 |
| JP | 2013-146555 A | 8/2013 |
| JP | 2015-123336 A | 7/2015 |
| RU | 2 399 642 C2 | 9/2010 |
| RU | 2 497 487 C2 | 11/2013 |

OTHER PUBLICATIONS

Office Action and Search Report dated Feb. 12, 2019 in the corresponding Russian Patent Application No. 2018106241 with English Translation of the Office Action and English Translation of Category of Cited Documents 16 pages.

* cited by examiner

HEATING TOOL

TECHNICAL FIELD

The present invention relates to a heating tool.

BACKGROUND ART

In the related art, there is a heating element that generates heat by an oxidation reaction of an oxidizable metal. The heat generating elements that are configured to contain the oxidizable metal such as iron powder, a carbon component, and water, and that generate heat by the oxidation reaction of the oxidizable metal are disclosed in, for example, Patent Documents 1 and 2.

In Patent Document 1, a heating element using an ink-like or creamy heat generation composition is described. According to the heating element, a generation of dust at the time of manufacturing the heating element is prevented, and a heat generation reaction of a heat generation composition is suppressed, so that it is said that it is possible to prevent loss due to the heat generation reaction at the time of manufacturing, and quality deterioration or solidification of the heat generation composition.

In Patent Document 2, a heating element in which blending of a heat generating layer and a water retaining layer is suitably controlled is described. According to the heating element, abnormal heat generation is prevented even in a case where a heat generation composition is filled in a large amount for some reason or is unevenly distributed in specific locations at the time of manufacturing the heating element, so that it is described that favorable heat generation characteristics can be stably obtained, and that it may be accompanied by generation of steam.

RELATED DOCUMENT

Patent Document

[Patent Document 1] Japanese Unexamined Patent Publication NO. H09-75388
[Patent Document 2] Japanese Unexamined Patent Publication NO. 2013-146555

SUMMARY OF THE INVENTION

That is, the present invention relates to a heating tool that includes a steam generator that a heat generating layer which contains an oxidizable metal, a carbon component, a water absorbent polymer, and water, and a water absorbent sheet which carries water are laminated, and a bag at least a portion of which has an air permeability and which accommodates the steam generator, in which a mass ratio of the water absorbent sheet is equal to or greater than 0.9 and equal to or less than 15 with respect to the water absorbent polymer contained in the heat generating layer.

In addition, the present invention relates to a heating tool that includes a steam generator having a heat generating layer which contains an oxidizable metal, a carbon component, a water absorbent polymer, and water, laminated with a water absorbent sheet which carries water, and a bag at least a portion of which has an air permeability and which accommodates the steam generator, wherein a basis weight of the water absorbent polymer contained in the heat generating layer is equal to or greater than 20 g/m$^2$ and equal to or less than 100 g/m$^2$ in a dry state, and a basis weight of the water absorbent sheet is equal to or greater than 50 g/m$^2$ and equal to or less than 500 g/m$^2$ in a dry state.

BRIEF DESCRIPTION OF THE DRAWINGS

The above and other objects, advantages and features will be more apparent from the following description of the preferred embodiments and the accompanying drawings.

DESCRIPTION OF EMBODIMENTS

Figure 1:
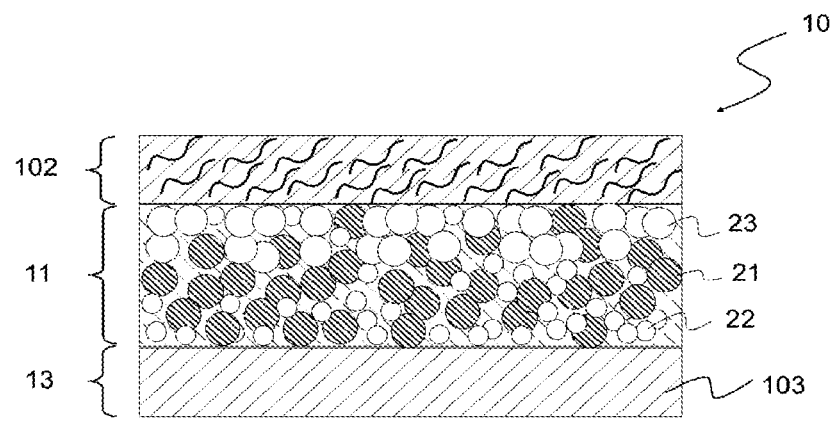
FIG. 1 is a cross-sectional view schematically showing a steam generator used in an embodiment.

Hereinafter, embodiments of the present invention will be described with reference to the drawings. In all the drawings, similar components are denoted by the same reference numerals, and description thereof will not be appropriately repeated. In addition, in the present specification, "to" represents "equal to or greater than and equal to or less than", unless otherwise specified.

The present inventors studied, and as a result, it was found that there is room for improvement in the following points, in a case where a heating element such as the above-described prior art document is to be of a type which stably generates steam.

That is, in the heating tool described in Patent Document 2, a polymer sheet obtained by laminating and integrating a paper having wood pulp, and a water absorbent polymer and the paper having wood pulp on a heat generating layer is used as a first water absorbent sheet. Although this configuration is excellent in that it does not cause abnormal heat generation even if there are manufacturing conditions and fluctuation of raw material components, it is found that there is a limit in terms of generating steam without increasing the temperature.

The present inventors studied on this point, and as a result, it was found that there is room for improvement in that it is difficult to convert the heat generated by the heat generating layer into steam, since the water absorbent polymer and the heat generating layer are disposed through the paper having wood pulp. In addition, since the paper having wood pulp is present between the water absorbent polymer and the heat generating layer as described above, it is difficult for water to be supplied to the heat generating layer. As a result, it was found that there is room for improvement in that the temperature as the heating element becomes unnecessarily high in some cases in a case of generating a large amount of steam.

On the other hand, Patent Document 1 discloses a technique of manufacturing a heating element by spraying a water absorbing agent on a heat generation composition to form a water absorbing layer. However, when moisture is contained in a large amount in order to generate steam, if merely spraying the water absorbing agent on the heat generation composition, it was found that there are problems that the amount of moisture in the heat generating layer increases and it is difficult to generate heat, the rising of the temperature as the heating element is delayed, and the amount of steam generated decreases.

The present invention is made in view of the background art as described above, and provides a heating tool which has a rapid rising in temperature, generates steam stably, and is likely to be controlled to an appropriate temperature.

The present inventors have found that the heating tool which has a rapid rising in temperature, generates steam stably, and is likely to be controlled to an appropriate temperature can be provided by accommodating a steam generator in which a heat generating layer containing an oxidizable metal, a carbon component, a water absorbent polymer, and water, and a water absorbent sheet having a specific maximum absorbing capacity are laminated is contained in a bag configured to include an air permeable sheet.

According to the heating tool of the present embodiment, the heating tool which generates the steam stably and which skin temperature is easily controlled to an appropriate temperature is provided.

FIG. 1 is a cross-sectional view schematically showing a steam generator 10 used in an embodiment. The steam generator 10 is configured to layers of a heat generating layer 11 and a water absorbent sheet 102, and in FIG. 1, a base material layer 13 (base material 103) is further provided separately. The heat generating layer 11 contains the oxidizable metal 21, the carbon component 22, the water absorbent polymer 23, and water.

The steam generator 10 generates heat by an oxidation reaction of an oxidizable metal 21 to impart a sufficient thermal effect, and can have a performance of, for example, a heat generation temperature of 38° C. to 70° C. in a measurement according to JIS standard S4100.

The oxidizable metal 21 is a metal that generates heat of oxidation reaction, and examples thereof include one or more kinds of powders or fibers selected from the group consisting of iron, aluminum, zinc, manganese, magnesium, and calcium. Among these, iron powder is preferable from the viewpoints of ease of handling, safety, manufacturing cost, storage stability, and stability. Examples of the iron powder include one or more kinds selected from the group consisting of reduced iron powder and atomized iron powder.

In a case where the oxidizable metal 21 is powder, from the viewpoint that the oxidation reaction is efficiently performed, the average particle diameter thereof is preferably equal to or greater than 10 μm and equal to or less than 200 μm, and more preferably equal to or greater than 20 μm and equal to or less than 150 μm. The particle diameter of the oxidizable metal 21 refers to the maximum length in the form of powder, and is measured by a classification with a sieve, a dynamic light scattering method, a laser diffraction method, or the like. Among these, in the present embodiment, it is preferable that the particle diameter of the oxidizable metal 21 is measured by a laser diffraction method.

From the same viewpoint, the average particle diameter of the oxidizable metal 21 is preferably equal to or greater than 10 μm, and more preferably equal to or greater than 20 μm. In addition, the average particle diameter of the oxidizable metal 21 is preferably equal to or less than 200 μm, and more preferably equal to or less than 150 μm.

The content of the oxidizable metal 21 in the heat generating layer 11 is preferably equal to or greater than 100 $g/m^2$ and equal to or less than 3,000 $g/m^2$, and more preferably equal to or greater than 200 $g/m^2$ and equal to or less than 1,500 $g/m^2$ in terms of basis weight. As a result, the heat generation temperature of the steam generator 10 can be raised to a desired temperature. Here, the content of the oxidizable metal 21 in the steam generator 10 can be determined by an ash test according to JIS P8128 or a thermogravimetric instrument. In addition, the content can be quantified by a magnetization measurement test with vibration sample type, or the like utilizing the property that magnetization occurs when an external magnetic field is applied. Among these, in the present embodiment, it is preferable to determine the content of the oxidizable metal 21 with the thermogravimetric instrument.

From the same viewpoint, the content of the oxidizable metal 21 in the heat generating layer 11 is preferably equal to or greater than 100 $g/m^2$, and more preferably equal to or greater than 200 $g/m^2$ in terms of basis weight. In addition, the content is preferably equal to or less than 3,000 $g/m^2$, and more preferably equal to or less than 1,500 $g/m^2$.

As the carbon component 22, although one having water retention capability, oxygen supply capability, and catalytic capability, and for example, one or more kinds selected from the group consisting of activated carbon, acetylene black, and graphite can be used, from the viewpoint of easiness of adsorbing oxygen when wet, and keeping moisture of the heat generating layer 11 constant, and from the viewpoint of easily controlling the amount of water carried on the water absorbent sheet 102 within a specific range, activated carbon is preferably used. More preferably, one or more kinds of fine powdery substances or small granules selected from the group consisting of coconut shell charcoal, wood charcoal powder, and peat coal are used. Among these, the wood charcoal powder is preferable in order to easily maintain the amount of water carried in the water absorbent sheet 102 within a specific range.

From the viewpoint of uniformly mixing with the oxidizable metal 21, and from the viewpoint of being likely to maintain the amount of water carried in the water absorbent sheet 102 within a specific range, the average particle diameter of the carbon component 22 is preferably equal to or greater than 10 μm and equal to or less than 200 μm, and more preferably equal to or greater than 12 μm and equal to or less than 100 μm. The average particle diameter of the carbon component 22 refers to the maximum length in the form of powder, and is measured by a dynamic light scattering method, a laser diffraction method, or the like. Among these, in the present embodiment, it is preferable that the average particle diameter of the carbon component 22 is measured by a laser diffraction method.

Although it is preferable to use a powdery form of the carbon component 22, it is possible to use a form other than a powdery form, for example, a fibrous form can be used.

From the same viewpoint, the average particle diameter of the carbon component 22 is preferably equal to or greater than 10 μm, and more preferably equal to or greater than 12 μm. In addition, the average particle diameter of the carbon component 22 is preferably equal to or less than 200 μm, and more preferably equal to or less than 100 μm.

The content of the carbon component 22 in the heat generating layer 11 is preferably equal to or greater than 0.3 parts by mass and equal to or less than 20 parts by mass, more preferably equal to or greater than 1 part by mass and equal to or less than 15 parts by mass, and still more preferably equal to or greater than 3 parts by mass and equal to or less than 13 parts by mass with respect to 100 parts by mass of the content of the oxidizable metal 21. In this manner, moisture necessary for sustaining the oxidation reaction can be accumulated in the obtained steam generator 10. In addition, the heating tool in which a sufficient amount of oxygen can be supplied to the steam generator 10, and which has high heat generation efficiency can be obtained. In addition, since the heat capacity of the steam generator 10 with respect to the obtained heat generation. value can be suppressed to be small, the rise in the heat generation temperature increases and a desired temperature rise can be obtained.

In addition, the content of the carbon component 22 in the heat generating layer 11 is preferably equal to or greater than 0.3 parts by mass, more preferably equal to or greater than 1 part by mass, and still more preferably equal to or greater than 3 parts by mass with respect to 100 parts by mass of the content of the oxidizable metal 21. In addition, the content of the carbon component 22 in the heat generating layer 11 is preferably equal to or less than 20 parts by mass, more preferably equal to or less than 15 part by mass, and still more preferably equal to or less than 13 parts by mass with respect to 100 parts by mass of the content of the oxidizable metal 21.

The content of the carbon component 22 in the heat generating layer 11 is preferably equal to or greater than 4 g/m$^2$ and equal to or less than 290 g/m$^2$, and more preferably equal to or greater than 7 g/m$^2$ and equal to or less than 160 g/m$^2$ in terms of basis weight.

In addition, the content of the carbon component 22 in the heat generating layer 11 is preferably equal to or greater than 4 g/m$^2$, and more preferably equal to or greater than 7 g/m$^2$ in terms of basis weight. In addition, the content of the carbon component 22 in the heat generating layer 11 is preferably equal to or less than 290 g/m$^2$, and more preferably equal to or less than 160 g/m$^2$ in terms of basis weight.

As the water absorbent polymer 23, a hydrophilic polymer having a crosslinked structure capable of absorbing and retaining a liquid equal to or more than 20 times its own weight can be included. Examples of the shape of the water absorbent polymer 23 include one or more kinds selected from the group consisting of a spherical shape, a lumpy shape, a grape-like shape, and a fibrous shape. The mass average particle diameter of the water absorbent polymer 23 is preferably equal to or greater than 1 µm and equal to or less than 1,000 µm, and more preferably equal to or greater than 10 µm and equal to or less than 500 µm. The particle diameter of the water absorbent polymer 23 is measured by a dynamic light scattering method, a laser diffraction method, or the like.

The mass average particle diameter of the water absorbent polymer 23 is preferably equal to or greater than 1 µm, and more preferably equal to or greater than 10 µm. In addition, the average particle diameter of the water absorbent polymer 23 is preferably equal to or less than 1,000 µm, and more preferably equal to or less than 500 µm.

Specific examples of the water absorbent polymer 23 include one or more kinds selected from the group consisting of starch, crosslinked carboxyl methylated cellulose, a polymer or copolymer of acrylic acid or an alkali metal salt of acrylic acid, and polyacrylic acid, a salt thereof, and a polyacrylate graft polymer. Among these, it is preferable to use a polymer or copolymer of acrylic acid or an alkali metal salt of acrylic acid, and polyacrylic acid, salt thereof, and polyacrylate graft polymer, because the amount of water carried in the water absorbent sheet 102 can be easily maintained within the specific range.

From the viewpoint of a rapid rising of the temperature of the steam generator 10, the content of the water absorbent polymer 23 in the heat generating layer 11 is preferably equal to or greater than 5 parts by mass, more preferably equal to or greater than 7 parts by mass, and still more preferably equal to or greater than 9 parts by mass with respect to 100 parts by mass of the content of the oxidizable metal 21. In addition, from the viewpoint of stably generating the steam, the content of the water absorbent polymer 23 in the heat generating layer 11 is preferably equal to or less than 20 parts by mass, more preferably equal to or less than 18 parts by mass, and still more preferably equal to or less than 16 parts by mass with respect to 100 parts by mass of the content of the oxidizable metal 21.

From the viewpoint of the rapid rising of the temperature of the steam generator 10, the basis weight of the water absorbent polymer 23 contained in the heat generating layer 11 is equal to or greater than 20 g/m$^2$, preferably equal to or greater than 25 g/m$^2$, and more preferably equal to or greater than 30 g/m$^2$ in a dry state. In addition, from the same viewpoint, the basis weight of the water absorbent polymer 23 contained in the heat generating layer 11 is equal to or less than 100 g/m$^2$, preferably equal to or less than 80 g/m$^2$, and more preferably equal to or less than 60 g/m$^2$ in a dry state. In addition, from the viewpoint of making the thickness of the heat generating layer 11 appropriate and improving the manufacturing efficiency, the basis weight of the water absorbent polymer 23 contained in the heat generating layer 11 in the dry state is equal to or greater than 20 g/m$^2$ and equal to or less than 100 g/m$^2$, preferably equal to or greater than 25 g/m$^2$ and equal to or less than 80 g/m$^2$, and more preferably equal to or greater than 30 g/m$^2$ and equal to or less than 60 g/m$^2$.

Although the water absorbent polymer 23 may be uniformly present in the heat generating layer 11, from the viewpoint of the rapid rising of the temperature of the steam generator 10 and stably generating the steam, as shown in FIG. 1, it is preferable that the water absorbent polymer 23 is disposed so as to be in contact with the water absorbent sheet 102. In order to dispose in this manner, for example, the water absorbent polymer 23 is laminated on one surface of the heat generating layer 11, and is disposed on the surface of the heat generating layer 11 on the side in contact with the water absorbent sheet 102 in a substantially sheet-like shape. Although a method of laminating may be appropriately selected from known methods, for example, it is possible to adopt a method in which the water absorbent polymer 23 is sprayed onto a layer containing a substance other than the water absorbent polymer 23 by a spraying method or the like, and thereafter the water absorbent sheet 102 is laminated.

As shown in FIG. 1, it is not necessary that the entire water absorbent polymer 23 is in contact with the water absorbent sheet 102, and at least a portion of the water absorbent polymer 23 may be in contact with the water absorbent sheet 102. In addition, the oxidizable metal 21 and the carbon component 22 may partially be in contact with the water absorbent sheet 102.

In addition, in the heat generating layer 11, for the purpose of improving the water absorbing property, a powder having water absorbing property can be used in combination. As the powder having the water absorbing property, one or more kinds selected from vermiculite, sawdust, silica gel, and pulp powder can be included.

From the viewpoint of stably generating the steam, the content of water in the heat generating layer 11 is preferably equal to or greater than 12% by mass, more preferably equal to or greater than 13% by mass, and still more preferably equal to or greater than 15% by mass. In addition, from the viewpoint of the rapid rising of the temperature of the steam generator, the content of water in the heat generating layer 11 is preferably equal to or less than 28% by mass, more preferably equal to or less than 27% by mass, and still more preferably equal to or less than 25% by mass.

The content of water in the heat generating layer 11 can be calculated, for example, by collecting approximately 1 g of the heat generating layer, precisely weighing the mass, and thereafter measuring the mass after drying the collected heat generating layer, and dividing the mass difference by the mass of the collected heat generating layer. Numerical values can be represented as a percentage as described above. Drying conditions can be, for example, 150° C. for 10 minutes.

From the viewpoint of the rapid rising of the temperature of the steam generator, the large amount of steam generated, and ease of temperature control, in the heat generating layer 11, the mass proportion (water/carbon component) of the content of water to the content of the carbon component 22 is preferably equal to or greater than 0.5, more preferably equal to or greater than 0.6, and still more preferably equal to or greater than 1. In addition, the mass proportion (water/carbon component) of the content of water to the content of the carbon component 22 is preferably equal to or less than 8.3, more preferably equal to or less than 7.7, and still more preferably equal to or less than 6.4.

Furthermore, since the air permeability of the steam generator 10 is sufficiently ensured, the steam generator having sufficient supply of oxygen and high heat generation efficiency can be obtained. In addition, since the heat capacity of the steam generator can be suppressed to be small with respect to the obtained heat generation value, the rise in the heat generation temperature increases and a desired temperature rise can be obtained.

From the viewpoint of the rapid rising of the temperature of the steam generator, in the heat generating layer 11, the mass proportion (water absorbent polymer/carbon component) of the water absorbent polymer 23 to the content of the carbon component 22 is preferably equal to or greater than 0.4, more preferably equal to or greater than 0.8, and still more preferably equal to or greater than 1.1. In addition, from the viewpoint of ease of temperature control, the mass proportion (water absorbent polymer/carbon component) of the water absorbent polymer 23 to the content of the carbon component 22 is preferably equal to or less than 5, more preferably equal to or less than 3.5, and still more preferably equal to or less than 2.5.

The heat generating layer 11 can further contain a reaction accelerator. By including the reaction accelerator, it is possible to be likely to sustain the oxidation reaction of the oxidizable metal 21. In addition, by using the reaction accelerator, it is possible to promote the oxidation reaction by destroying the oxide film formed on the oxidizable metal 21 accompanying the oxidation reaction. Examples of the reaction accelerator include one or more kinds selected from the group consisting of alkali metal, alkaline earth metal sulfate, and chloride. Among these, from the viewpoint of excellent conductivity, chemical stability, and production cost, one or more kinds selected from the group consisting of various chlorides such as sodium chloride, potassium chloride, calcium chloride, magnesium chloride, primary iron chloride, secondary ferric chloride, and sodium sulfate are preferably used.

From the viewpoint that a sufficient heat generation value lasts for a long time, the content of the reaction accelerator in the heat generating layer 11 is preferably equal to or greater than 2 parts by mass and equal to or less than 15 parts by mass, and more preferably equal to or greater than 3 parts by mass and equal to or less than 13 parts by mass with respect to 100 parts by mass of the content of the oxidizable metal 21.

From the same viewpoint, the content of the reaction accelerator in the heat generating layer 11 is preferably equal to or greater than 2 parts by mass, and more preferably equal to or greater than 3 parts by mass with respect to 100 parts by mass of the content of the oxidizable metal 21. In addition, the content of the reaction accelerator in the heat generating layer 11 is preferably equal to or less than 15 parts by mass, and more preferably equal to or less than 13 parts by mass with respect to 100 parts by mass of the content of the oxidizable metal 21.

The heat generating layer 11 can further contain a thickener. As the thickener, the thickener absorbs moisture to increase consistency, or a substance imparting thixotropy can be used, and one or more kinds of mixtures selected from polysaccharide based thickeners such as alginate such as sodium alginate, gum arabic, gum tragacanth, locust bean gum, guar gum, arabic gum, carrageenan, agar, xanthan gum; starch based thickeners such as dextrin, pregelatinized starch, processing starches; cellulose derivative type thickeners such as carboxymethyl cellulose, ethyl cellulose acetate, hydroxyethyl cellulose, hydroxymethyl cellulose, or hydroxypropyl cellulose; metal soap based thickeners such as stearate; mineral based thickeners such as bentonite, and the like, can be mainly used.

Among these, from the viewpoint of an excellent coating performance and maintaining the amount of water carried in the water absorbent sheet 102 at specific value, a polysaccharide based thickener is preferable, and a polysaccharide based thickener having a molecular weight of equal to or greater than 1,000,000 and equal to or less than 50,000,000 is more preferable, and a polysaccharide based thickener having a molecular weight of equal to or greater than 1,5000,000 and equal to or less than 40,000,000 is still more preferable. In addition, from the viewpoint of having excellent coating performance and salt resistance, xanthan gum is preferable.

The content of the thickener in the heat generating layer 11 is preferably equal to or greater than 0.05 parts by mass and equal to or less than 5 parts by mass, and more preferably equal to or greater than 0.1 parts by mass and equal to or less than 4 parts by mass with respect to 100 parts by mass of the content of the oxidizable metal 21. Within this range, it is possible to stably disperse the solid contents of the oxidizable metal 21, the carbon component 22, and the like. In addition, thixotropy can be imparted, and the coating performance can be further improved. Furthermore, the amount of water carried in the water absorbent sheet 102 can be easily maintained within a specific range, which is preferable.

From the same viewpoint, the content of the thickener in the heat generating layer 11 is preferably equal to or greater than 0.05 parts by mass, and more preferably equal to or greater than 0.1 parts by mass with respect to 100 parts by mass of the content of the oxidizable metal 21. In addition, the content of the thickener in the heat generating layer 11 is preferably equal to or less than 5 parts by mass, and more preferably equal to or less than 4 parts by mass with respect to 100 parts by mass of the content of the oxidizable metal 21.

The heat generating layer 11 may contain a surfactant, a chemical agent, a flocculant, a colorant, a paper strength enhancer, a pH adjuster, a bulking agent, and the like, if necessary.

Subsequently, the water absorbent sheet 102 provided in the steam generator 10 of the present embodiment will be described.

From the viewpoint of the rapid rising of the temperature of the steam generator, stability of steam generation, and ease of temperature control, a maximum water absorbing capacity of the water absorbent sheet 102 is preferably equal to or greater than 0.1 g/cm², more preferably equal to or greater than 0.15 g/cm², still more preferably equal to or greater than 0.2 g/cm², still more preferably equal to or greater than 0.5 g/cm², and even more preferably equal to or greater than 0.7 g/cm². In addition, from the same viewpoint, it is preferably equal to or less than 5 g/cm², more preferably equal to or less than 4 g/cm², and still more preferably equal to or less than 3 g/cm². In the present invention, the maximum water absorbing capacity of the water absorbent sheet 102 is measured by the following method.

[Method for Measuring Maximum Water Absorbing Capacity ($Z_{max}$) of Water Absorbent Sheet]

Only the water absorbent sheet is peeled from the steam generator, is washed with ion exchanged water, and thereafter is heated and dried at 80° C. for 10 minutes. After drying, the water absorbent sheet is cut to a size of approximately 5 cm square, the area (S) [cm²] and the mass ($W_0$) [g] are measured, and the absorbent sheet is immersed in a 5% by mass sodium chloride aqueous solution for 5 minutes. Thereafter, the water absorbent sheet is taken out with tweezers, and hung in the air for 5 minutes to drip and drop the water that the water absorbent sheet cannot hold. Thereafter, the mass ($W_1$) [g] is measured, and the maximum water absorbing capacity ($Z_{max}$) [g/cm²] of the water absorbent sheet is calculated from the following Formula (1).

$$Z_{max}=(W_1-W_0)/S \quad \text{(Formula 1)}$$

Here, from the viewpoint of the rapid rising of the temperature of the steam generator, and the stability of steam generation, the amount of water carried in the water absorbent sheet 102 is preferably equal to or greater than 28 g/m², more preferably equal to or greater than 30 g/m², and still more preferably equal to or greater than 35 g/m² in terms of basis weight. In addition, from the viewpoint of ease of temperature control, the amount of water carried in the water absorbent sheet 102 is preferably equal to or less than 150 g/m², more preferably equal to or less than 140 g/m², and still more preferably equal to or less than 130 g/m² in terms of basis weight.

The content of water carried in the water absorbent sheet 102 can be calculated, for example, by peeling off only the water absorbent sheet from the steam generator, measuring the area and the mass, and thereafter measuring the mass after drying the peeled water absorbent sheet, and dividing the mass difference by the area of the water absorbent sheet. The numerical value can be represented in basis weight as described above. Drying conditions can be, for example, at 80° C. for 10 minutes. The "area of the water absorbent sheet" as used herein refers to the area of the water absorbent sheet in the portion laminated on the heat generating layer. For example, in a case where the area of the heat generating layer is smaller than the area of the water absorbent sheet, the area of the water absorbent sheet overlapping with the heat generating layer is calculated.

Although the mass ratio of the water absorbent sheet 102 to the water absorbent polymer 23 contained in the heat generating layer 11 is equal to or greater than 0.9 and equal to or less than 15, it is preferably equal to or greater than 1.5, and more preferably equal to or greater than 2, from the viewpoint of the rapid rising of the temperature of the steam generator. In addition, from the viewpoint of stably generating the steam, it is preferably equal to or less than 13, and more preferably equal to or less than 10.

As described above, Patent Document 1 discloses a technique of dispersing the water absorbing agent on the heat generation composition to form the water absorbing layer. However, when moisture is contained in a large amount in order to generate steam, if merely spraying the water absorbing agent on the heat generation composition, there are problems that the amount of moisture in the heat generating layer increases and it is difficult to generate heat, the rising of the temperature as the heating element is delayed, and the amount of steam generated decreases. On the other hand, it is conceivable to coat the upper surface of the water absorbing agent with other material in order to improve the rising of the temperature as the heating element, but there is a concern that the material to be coated hinders the passage of oxygen and consequently suppresses the generation of the steam.

That is, the mass ratio of the water absorbent sheet 102 to the water absorbent polymer 23 is appropriately set as described above, so that it is possible to effectively improve the rising of the temperature as the steam generator, and in addition, to appropriately improve the steam generation amount.

In addition, the basis weight of the water absorbent polymer 23 contained in the heat generating layer 11 in the dry state and the basis weight of the water absorbent sheet 102 in the dry state described later are combined and are appropriately controlled. Therefore, it is possible to improve the handling property by appropriately setting the thickness of the heating tool 100, to efficiently impart the thermal effect, and to improve the manufacturing efficiency.

For example, the water absorbent sheet 102 may be configured to include a single fiber sheet, or two or more layers thereof may be laminated.

Specific examples of the water absorbent sheet 102 include a paper, a nonwoven fabric, a laminated sheet of paper and nonwoven fabric, and the like, which are produced from fiber materials described later. In addition, sheet material such as papermaking and nonwoven fabric in which other fiber material is further laminated or mixed on the fiber material such as pulp fiber and rayon fiber, may be used.

By using such a water absorbent sheet 102, it is easy to set the amount of water carried in the sheet within the specific range, the rising of the temperature of the steam generator can be made earlier, and the generated steam can be effectively discharged, which are preferable.

As the above fiber material, either a hydrophilic fiber or a hydrophobic fiber can be used, and it is preferable to use the hydrophilic fiber. Among these, it is more preferable to use a cellulose fiber because it is easy to set the amount of water carried in the water absorbent sheet 102 within the specific range, and the generated steam can be effectively discharged. As the cellulose fiber, chemical fiber (synthetic fiber) or natural fiber can be used.

As the chemical fiber of the cellulose fiber, for example, rayon or acetate can be used. On the other hand, as the natural fiber of the cellulose fiber, for example, one or more kinds selected from various kinds of plant fiber, wood pulp fiber, non-wood pulp fiber, cotton fiber, linen fiber, wheat straw fiber, hemp fiber, jute fiber, kapok fiber, coconut fiber, and juncus fiber can be used. It is preferable to use crepe paper using wood pulp fibers among these cellulose fibers, because it is easy to set the amount of water carried in the water absorbent sheet 102 within the specific range, and the generated steam can be effectively discharged.

The fiber length of various fiber materials is preferably equal to or greater than 0.5 mm and equal to or less than 6 mm, and more preferably equal to or greater than 0.8 mm and equal to or less than 4 mm. In addition, the fiber length of fiber materials is preferably equal to or greater than 0.5 mm, and more preferably equal to or greater than 0.8 mm.

In addition, the fiber length of fiber materials is preferably equal to or less than 6 mm, and more preferably equal to or less than 4 mm.

In addition to the hydrophilic fiber, the hydrophobic fiber, especially a heat fusible fiber may be blended into the water absorbent sheet 102, if necessary. In a case of blending the heat fusible fibers, the blending amount is preferably equal to or greater than 0.1% by mass and equal to or less than 10% by mass, and more preferably equal to or greater than 0.5% by mass and equal to or less than 5% by mass with respect to the total amount of the fibers in the water absorbent sheet 102.

From the same viewpoint, the blending amount of the heat fusible fibers is preferably equal to or greater than 0.1% by mass, and more preferably equal to or greater than 0.5% by mass with respect to the total amount of the fibers in the water absorbent sheet 102. In addition, the blending amount of the heat fusible fibers is preferably equal to or less than 10% by mass, and more preferably equal to or less than 5% by mass with respect to the total amount of the fibers in the water absorbent sheet 102.

In addition, the water absorbent sheet 102 is preferably an air-permeable sheet, but is normally set to a value sufficiently smaller than a degree of air permeability value of a first bag sheet 20a described later.

From the viewpoint that the amount of water carried in the sheet can be easily adjusted to a specific range, the basis weight of the water absorbent sheet 102 in a dry state is equal to or greater than 50 g/m$^2$, preferably equal to or greater than 100 g/m$^2$, and more preferably equal to or greater than 150 g/m$^2$. In addition, the basis weight of the water absorbent sheet 102 in a dry state is equal to or less than 500 g/m$^2$, preferably equal to or less than 400 g/m$^2$, and more preferably equal to or less than 300 g/m$^2$. In addition, from the viewpoint of making the thickness of the water absorbent sheet 102 appropriate and improving the manufacturing efficiency, the basis weight of the water absorbent sheet 102 in a dry state is equal to or greater than 50 g/m$^2$ and equal to or less than 500 g/m$^2$, preferably equal to or greater than 100 g/m$^2$ and equal to or less than 400 g/m$^2$, and more preferably equal to or greater than 150 g/m$^2$ and equal to or less than 300 g/m$^2$.

As a specific aspect of the steam generator 10 of the present embodiment, separately from the water absorbent sheet 102, other base material layer 13 is provided, and the heat generating layer 11 is interposed between the water absorbent sheet 102 and the base material layer 13 to form a so-called sandwich structure.

Here, as the base material layer 13, although it can be appropriately set according to the use of the heating tool to be manufactured, it is configured to normally include a material having poor water absorbing property, and it can be configured to include, for example, a synthetic resin film. More specifically, a polyethylene film, a polyethylene terephthalate film, a Teflon (registered trademark) film, or the like can be used.

Here, the effects of the steam generator 10 of the present embodiment will be described. The steam generator 10 of the present embodiment has a structure in which the heat generating layer 11 and the water absorbent sheet 102 are laminated.

According to adopting this structure, moisture is present in the vicinity of the heat generating layer 11, so that the heat energy generated by the heat generating layer 11 is likely to be effectively changed into steam. In addition, an effect that the temperature does not become too high due to appropriate water supply from the water absorbent sheet 102 is exerted.

In addition, since the water absorbent sheet 102 exhibits specific physical properties, it is easy to supply external oxygen to the heat generating layer 11, and it is possible to prevent the heat energy that the heat generating layer 11 generated from escaping to the outside.

As a result, the steam generator 10 of the present embodiment can realize the characteristic that the rising of the temperature is fast, steam is generated stably, and it is easy to control to an appropriate temperature.

In addition, although the steam generator 10 of the present embodiment has a structure in which the heat generating layer 11 and the water absorbent sheet 102 are laminated, it is preferable that the water absorbent sheet 102 is positioned on the skin side of the user of the heating tool 100 and the heat generating layer 11 is positioned on the side opposite to the skin side of the user. As a result, the above-described characteristics can be effectively imparted to the user.

Next, an example of a method for manufacturing the steam generator 10 will be described. For example, the steam generator 10 can be prepared by coating an oxidizable metal 21, a carbon component 22, and an aqueous dispersion of heat generation powders containing water or the like to the base material layer 13, and thereafter, by spraying the water absorbent polymer 23 on the layer of the coated heat generation powder aqueous dispersion, and finally disposing the water absorbent sheet 102 on the sprayed water absorbent polymer 23.

Although the aqueous dispersion of heat generation powders may be prepared by mixing all of the above-described components at once, an aqueous solution is previously prepared by dissolving a reaction accelerator in a solution prepared by dissolving a thickener in water, and thereafter the premixed solution of the oxidizable metal 21 and the carbon component 22 may be mixed with the aqueous solution.

Although the reaction accelerator may be simultaneously mixed with other components in the aqueous dispersion of heat generation powders, a reaction accelerator which is separately dissolved in water or the like after the aqueous dispersion of heat generation powders is coated may be added by penetrating, spraying or dropping, and powders of the reaction accelerator may be sparged.

The water absorbent polymer 23 is sprayed on the layer of the aqueous dispersion of heat generation powders. Furthermore, in the stage of disposing the water absorbent sheet 102, water is partially absorbed in the water absorbent polymer 23 and the water absorbent sheet 102, and the heat generating layer 11 is formed.

That is, the heat generating layer 11 is configured to include the remaining components which are not absorbed by the water absorbent sheet 102.

Figure 2:
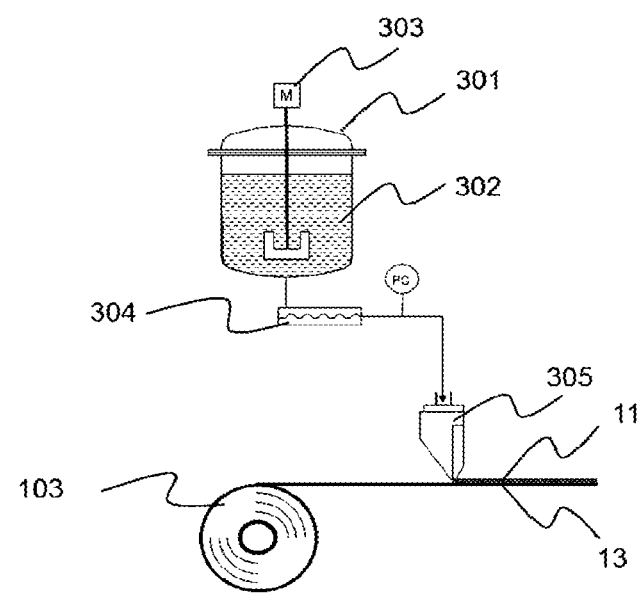
FIG. 2 is a view which describes a method for manufacturing the steam generator used in the embodiment.

FIG. 2 is a view which more specifically describes the method for manufacturing. First, an aqueous dispersion of heat generation powders 302 containing an oxidizable metal 21, a carbon component 22, water and the like is prepared in a coating tank 301. The aqueous dispersion of heat generation powders 302 may be stirred with a stirrer 303 to more uniformly disperse water-insoluble components such as the oxidizable metal 21 and the carbon component 22. Although the aqueous dispersion of heat generation powders 302 may be prepared by mixing all of the above-described components at once, an aqueous solution is previously prepared by dissolving a reaction accelerator in a solution prepared by dissolving a thickener in water, and thereafter the premixed solution of the oxidizable metal 21 and the carbon component 22 may be mixed with the aqueous solution.

Thereafter, the aqueous dispersion of heat generation powders 302 is pumped up to a die head 305 by a pump 304. The aqueous dispersion of heat generation powders 302 which is pumped up is coated to a base material 103 while adding pressure and extruding using the die head 305. At this time, the coating basis weight of the aqueous dispersion of heat generation powders 302 is preferably equal to or greater than 160 g/m$^2$ and equal to or less than 4,800 g/m$^2$, and more preferably equal to or greater than 320 g/m$^2$ and equal to or less than 2,200 g/m$^2$.

In FIG. 2, coating by die coating is exemplified, but the coating method is not limited thereto, and for example, roll coating, screen printing, roll gravure, knife coating, curtain coater, and the like can be used.

According to the above procedure, since a continuous long object having the heat generating layer 11 and the base material 103 can be obtained, the water absorbent polymer 23 is sprayed thereon, and finally the water absorbent sheet 102 is laminated thereon, so that a laminate is obtained. Finally, by cutting the laminate to an arbitrary size, the steam generator 10 is formed.

In the above method, in order to suppress the oxidation of the oxidizable metal 21 in the manufacturing process, a means for keeping the oxidizable metal 21 in a non-oxidizing atmosphere may be used if necessary.

Figure 3:
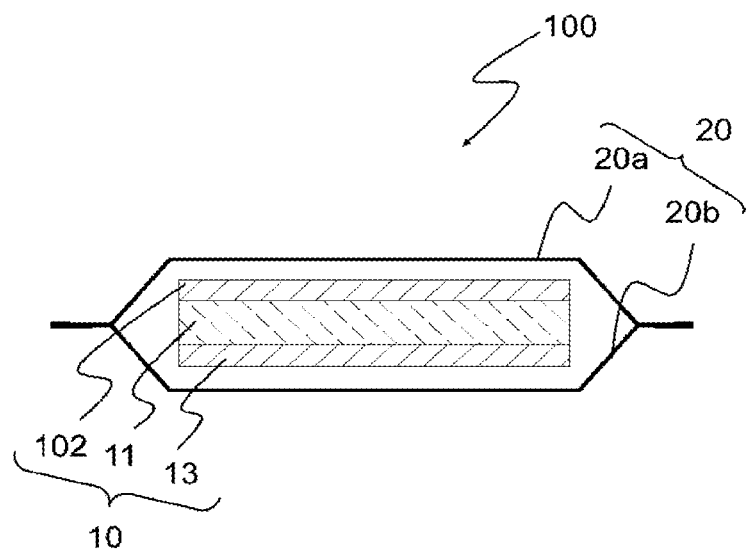
FIG. 3 is a cross-sectional view schematically showing an example of a heating tool according to an embodiment.

FIG. 3 is a schematic cross-sectional view showing an example of the heating tool provided with the steam generator 10 shown in FIG. 1. As shown in the drawing, the heating tool 100 is provided with the steam generator 10 having a sandwich structure in which a heat generating layer 11 is interposed between a water absorbent sheet 102 and a base material layer 13, and the bag 20 at least a portion of which has the air permeability and accommodates the steam generator 10.

More specifically, the heating tool 100 adopts a structure in which the steam generator 10 having the heat generating layer 11 and the water absorbent sheet 102 is placed in the bag 20 configured to include an air permeable sheet at least a portion of which has the air permeability, and the periphery of the bag 20 is bonded and sealed. In the heating tool 100, since the heat generating layer 11 is interposed between the water absorbent sheet 102 and the base material layer 13, it is possible to prevent the heat generating layer 11 from adhering to the bag 20.

The bag 20 is preferably configured to include a first bag sheet 20a and a second bag sheet 20b.

It is preferable that each of the first bag sheet 20a and the second bag sheet 20b has an extension region extending outward from the periphery of the steam generator 10, and are bonded to each other in each extension region. It is preferable that this bonding is a continuous airtight bonding at the periphery. The bag 20 formed by bonding the first bag sheet 20a and the second bag sheet 20b has a space for accommodating the steam generator 10 therein. The steam generator 10 is accommodated in this space. The steam generator 10 may be in a fixed state or may be in a non-fixed state to the bag 20.

A portion or an entire of the first bag sheet 20a has the air permeability. From the viewpoint of ease of temperature control, the degree of air permeability (JIS P8117, revised edition of 2009, all the same in this specification) of the first bag sheet 20a is preferably greater than 500 sec/100 mL, more preferably greater than 1,000 sec/100 mL, still more preferably greater than 1,200 sec/100 mL, and even more preferably equal to or greater than 1,500 sec/100 mL.

As the first bag sheet 20a having such degree of air permeability, for example, it is preferable to use a synthetic resin porous sheet having moisture permeability, but not having water permeability. Specifically, a film obtained by containing and stretching calcium carbonate or the like in polyethylene can be used. In a case of using such a porous sheet, various fiber sheets including one or more kinds of nonwoven fabrics selected from a needle-punched nonwoven fabric, an air-through nonwoven fabric, and a spunbonded nonwoven fabric may be laminated on the outer surface of the porous sheet to enhance the texture of the first bag sheet 20a. Although a portion or the entire of the first bag sheet 20a may be the air permeable sheet having the air permeability or a non-air permeable sheet not having the air permeability, it is preferable that the sheet is a sheet having higher air permeability than the second bag sheet 20b (that is, a sheet having low degree of air permeability).

From the viewpoint of the rapid rising of the temperature of the steam generator and the large amount of steam generated, the degree of air permeability of the first bag sheet 20a is preferably equal to or less than 10,000 sec/100 mL, more preferably equal to or less than 8,000 sec/100 mL, still more preferably equal to or less than 5,000 sec/100 mL, and even more preferably equal to or less than 4,000 sec/100 mL.

Although a portion or the entire of the second bag sheet 20b may be the air permeable sheet having the air permeability or a non-air permeable sheet not having the air permeability, it is preferable that the sheet is a sheet having lower air permeability than the first bag sheet 20a (that is, a sheet having high degree of air permeability). With such a configuration, as a heating tool for generating the steam, a larger amount of steam is generated from the first bag sheet 20a which is in contact with the water absorbent sheet 102 and a steam generating surface of the heating element, and an application site can be more efficiently heated when applying the heating tool to the body.

In a case where the second bag sheet 20b is a non-air permeable sheet, various fiber sheets including one or more kinds of nonwoven fabrics selected from a needle-punched nonwoven fabric, an air-through nonwoven fabric, and a spunbonded nonwoven fabric may be laminated on a film having one or multiple layers of synthetic resin or an outer surface of the film having one or multiple layers of synthetic resin to enhance the texture of the second bag sheet 20b. Specifically, a two-layer film including a polyethylene film and a polyethylene terephthalate film, a laminate film including a polyethylene film and a nonwoven fabric, a laminate film including a polyethylene film and a pulp sheet, and the like are used, and the laminate film including the polyethylene film and the pulp sheet is still more preferred.

In a case where the second bag sheet 20b is the air permeable sheet, although the same sheet as the first bag sheet 20a may be used or a different sheet from the first bag sheet 20a may be used, it is preferable that the sheet is a sheet having lower air permeability than the first bag sheet 20a (that is, a sheet having high degree of air permeability) as described above. In a case of using different sheets, on condition that the air permeability of the second bag sheet 20b is lower than the air permeability of the first bag sheet 20a, from the viewpoint of ease of temperature control, the degree of air permeability of the second bag sheet 20b is preferably equal to or greater than 5,000 sec/100 mL, and more preferably equal to or greater than 8,000 sec/100 mL.

In addition, from the viewpoint of the rapid rising of the temperature of the steam generator and the amount of steam generated from the first bag sheet 20a side, the degree of air permeability of the second bag sheet 20b is preferably equal to or less than 150,000 sec/100 mL, and more preferably equal to or less than 100,000 sec/100 mL.

When the steam generator 10 is accommodated in the bag 20, if the sheet and the layer are respectively inserted so that the water absorbent sheet 102 is on the side of the first bag sheet 20a and the base material layer 13 is on the side of the second bag sheet 20b and the peripheral edge portion is hermetically sealed, the oxidation reaction of the oxidizable metal 21 becomes favorable and it is possible to generate a large amount of the steam from the side of the first bag sheet 20a, which are preferable. In addition, in the heating tool which accommodates the steam generator 10 in the bag 20, it is preferable that the side of the first bag sheet 20a, that is, the side of the water absorbent sheet 102, is applied to the skin.

The steam generator 10 accommodated in the bag 20 may be one sheet or may be accommodated in a multilayer state in which a plurality of sheets are laminated.

As described above, although the bag 20 may be laminated with various fiber sheets in order to enhance the texture thereof, the bag 20 may be accommodated in an exterior body (not shown in the drawings) having the air permeability, so that the texture and the usability thereof may be enhanced. It is preferable that the exterior body is preferably configured to include a first exterior sheet and a second exterior sheet, one surface of the bag 20 is covered with the first exterior sheet, and the other surface of the bag 20 is covered with the second exterior sheet, and the first exterior sheet and the second exterior sheet are bonded, and preferably hermetically bonded, to each other in an extension region extending outward from the peripheral edge of the bag 20. As a result, a space for accommodating the bag 20 is formed inside the exterior body, and the steam generator 10 surrounded by the bag 20 can be accommodated in the space. The bag 20 may be in a fixed state or may be in a non-fixed state to the exterior body.

The degree of air permeability of the exterior body sheet, that is, the first exterior sheet and the second exterior sheet, is preferably set to equal to or less than 3,000 sec/100 mL, and more preferably equal to or greater than 1 sec/100 mL and equal to or less than 100 sec/100 mL on condition that it is higher than the air permeability of the first bag sheet 20a. By setting such degree of air permeability, the oxidation reaction of the oxidizable metal 21 becomes favorable and a large amount of the steam can be generated.

The first and second exterior sheets constituting the exterior body are not particularly limited in types, for example, such as various fiber sheets including a nonwoven fabric, as long as the sheets have the air permeability. For example, one or more kinds selected from a needle-punched nonwoven fabric, an air-through nonwoven fabric, and a spunbonded nonwoven fabric can be used.

The heating tool 100 has the bag 20 having the air permeability and the exterior body having the air permeability, so that the heating tool 100 can be a steam heating tool capable of generating the steam with the oxidation reaction of the oxidizable metal 21.

The heating tool 100 may have an adhesive layer (not shown in the drawings) formed by coating an adhesive compound on the outer surface of the exterior body, for example, the front surface of the first exterior sheet or the second exterior sheet constituting the exterior body. The adhesive layer is used for attaching the heating tool 100 to the skin, clothing, and the like of the human body. As the adhesive compound constituting the adhesive layer, the same materials as the adhesives used so far in the technical field including a hot-melt adhesive can be used.

It is preferable that the heating tool 100 is hermetically accommodated in a packaging bag (not shown in the drawings) having oxygen barrier properties until just before use.

The heating tool 100 is directly applied to a human body or attached to clothes, and is preferably used for warming the human body. Examples of application sites in the human body include a shoulder, a neck, an eye, a vicinity of eye, a waist, an elbow, a knee, a thigh, a lower thigh, an abdomen, a lower abdomen, hands, soles of feet, and the like. In addition to the human body, the warming tool 100 is applied to various goods and is preferably used for warming and keeping warm.

The above steam generator 10 can be used for other types of heating tools other than the type shown in FIG. 3, or for other uses.

Hereinbefore, although the embodiments of the present invention have been described with reference to the drawings, these are examples of the present invention, and various configurations other than those described above can be adopted.

Regarding the above embodiments, the present invention further discloses the following composition, manufacturing method, or application.

<1> A heating tool including a steam generator that a heat generating layer which contains an oxidizable metal, a carbon component, a water absorbent polymer, and water, and a water absorbent sheet which carries water are laminated, and a bag at least a portion of which has an air permeability and accommodates the steam generator, in which a mass ratio of the water absorbent sheet is equal to or greater than 0.9 and equal to or less than 15 with respect to the water absorbent polymer contained in the heat generating layer.

<2> The heating tool according to <1>, in which the amount of water carried in the water absorbent sheet is preferably equal to or greater than 28 g/m$^2$, more preferably equal to or greater than 30 g/m$^2$, and still more preferably equal to or greater than 35 g/m$^2$, and is preferably equal to or less than 150 g/m$^2$, more preferably equal to or less than 140 g/m$^2$, and still more preferably equal to or less than 130 g/m$^2$ in terms of basis weight.

<3> The heating tool according to <1> or <2>, in which the content of water in the heat generating layer is preferably equal to or greater than 12% by mass, more preferably equal to or greater than 13% by mass, and still more preferably equal to or greater than 15% by mass, and is preferably equal to or less than 28% by mass, more preferably equal to or less than 27% by mass, and still more preferably equal to or less than 25% by mass.

<4> The heating tool according to any one of <1> to <3>, in which the content of the water absorbent polymer in the heat generating layer is preferably equal to or greater than 5 parts by mass, more preferably equal to or greater than 7 parts by mass, and still more preferably equal to or greater than 9 parts by mass, and is preferably equal to or less than 20 parts by mass, more preferably equal to or less than 18 parts by mass, and still more preferably equal to or less than 16 parts by mass with respect to 100 parts by mass of a content of the oxidizable metal.

<5> The heating tool according to any one of <1> to <4>, in which the mass proportion of the content of the water absorbent polymer to a content of the carbon component (water absorbent polymer/carbon component) in the heat generating layer is preferably equal to or greater than 0.4, more preferably equal to or greater than 0.8, and still more preferably equal to or greater than 1.1, and is preferably equal to or less than 5, more preferably equal to or less than 3.5, and still more preferably equal to or less than 2.5.

<6> The heating tool according to any one of <1> to <5>, in which the basis weight of the water absorbent sheet in the dry state is preferably equal to or greater than 20 $g/m^2$, more preferably equal to or greater than 35 $g/m^2$, and still more preferably equal to or greater than 50 $g/m^2$, and is preferably equal to or less than 500 $g/m^2$, more preferably equal to or less than 450 $g/m^2$, and still more preferably equal to or less than 400 $g/m^2$.

<7> The heating tool according to any one of <1> to <6>, in which at least a portion of the water absorbent polymer is preferably disposed so as to be in contact with the water absorbent sheet.

<8> The heating tool according to any one of <1> to <7>, in which the content of the carbon component is preferably equal to or greater than 0.3 parts by mass, more preferably equal to or greater than 1 part by mass, and still more preferably equal to or greater than 3 parts by mass, and is preferably equal to or less than 20 parts by mass, more preferably equal to or less than 15 parts by mass, and still more preferably equal to or less than 13 parts by mass with respect to 100 parts by mass of the content of the oxidizable metal.

<9> The heating tool according to any one of <1> to <8>, in which the heat generating layer preferably further includes the thickener.

<10> The heating tool according to <9>, in which the thickener is preferably one or more kinds selected from polysaccharide based thickeners such as alginate such as sodium alginate, gum arabic, gum tragacanth, locust bean gum, guar gum, arabic gum, carrageenan, agar, xanthan gum; starch based thickeners such as dextrin, pregelatinized starch, processing starches; cellulose derivative type thickeners such as carboxymethyl cellulose, ethyl cellulose acetate, hydroxyethyl cellulose, hydroxymethyl cellulose, or hydroxypropyl cellulose; metal soap based thickeners such as stearate; mineral based thickeners such as bentonite, and the like, more preferably a polysaccharide based thickener, still more preferably a polysaccharide based thickener having a molecular weight of equal to or greater than 1,000,000 and equal to or less than 50,000,000, and even more preferably a polysaccharide based thickener having a molecular weight of equal to or greater than 1,5000,000 and equal to or less than 40,000,000.

<11> The heating tool according to <9> or <10>, in which a content of the thickener is preferably equal to or greater than 0.05 parts by mass, and more preferably equal to or greater than 0.1 part by mass, and is preferably equal to or less than 5 parts by mass, and more preferably equal to or less than 4 parts by mass with respect to 100 parts by mass of the oxidizable metal.

<12> The heating tool according to anyone of <1> to <11> further including an air permeable sheet in which the degree of air permeability of the bag accommodating the steam generator is preferably greater than 500 sec/100 mL, more preferably greater than 1,000 sec/100 mL, still more preferably greater than 1,200 sec/100 mL, and even more preferably equal to or greater than 1,500 sec/100 mL, and is preferably equal to or less than 10,000 sec/100 mL, more preferably equal to or less than 8,000 sec/100 mL, still more preferably equal to or less than 5,000 sec/100 mL, and even more preferably equal to or less than 4,000 sec/100 mL.

<13> The heating tool according to any one of <1> to <12>, in which the average particle diameter of the carbon component is preferably equal to or greater than 10 μm, and more preferably equal to or greater than 12 μm, and is preferably equal to or less than 200 μm, and more preferably equal to or less than 100 μm.

<14> The heating tool according to any one of <1> to <13>, in which a maximum water absorbing capacity of the water absorbent sheet is preferably equal to or greater than 0.1 $g/cm^2$, more preferably equal to or greater than 0.15 $g/cm^2$, still more preferably equal to or greater than 0.2 $g/cm^2$, still more preferably equal to or greater than 0.5 $g/cm^2$, and even more preferably equal to or greater than 0.7 $g/cm^2$, and is preferably equal to or less than 5 $g/cm^2$, more preferably equal to or less than 4 $g/cm^2$, and still more preferably equal to or less than 3 $g/cm^2$.

<15> The heating tool according to any one of <1> to <14>, in which the content of the oxidizable metal in the heat generating layer is preferably equal to or greater than 100 $g/m^2$, and more preferably equal to or greater than 200 $g/m^2$, and is preferably equal to or less than 3,000 $g/m^2$, and more preferably equal to or less than 1,500 $g/m^2$ in terms of basis weight.

<16> The heating tool according to any one of <1> to <15>, in which a mass proportion of the content of the water to a content of the carbon component (water/carbon component) in the heat generating layer is preferably equal to or greater than 0.5, more preferably equal to or greater than 0.6, and still more preferably equal to or greater than 1, and is preferably equal to or less than 8.3, more preferably equal to or less than 7.7, and still more preferably equal to or less than 6.4.

<17> The heating tool according to any one of <1> to <16>, in which the mass ratio of the water absorbent sheet is preferably equal to or greater than 1.5, and more preferably equal to or greater than 2, and is preferably equal to or less than 13, and more preferably equal to or less than 10 with respect to the water absorbent polymer contained in the heat generating layer.

<18> The heating tool according to any one of <1> to <17>, in which the bag accommodating the steam generator is preferably configured to include a first bag sheet and a second bag sheet, and is bonded in the extension region extending outward from the periphery of the steam generator.

<19> The heating tool according to <18>, in which a degree of air permeability of the first bag sheet is preferably lower than a degree of air permeability of the second bag sheet.

<20> The heating tool according to <18> or <19>, in which the degree of air permeability of the first bag sheet is preferably greater than 500 sec/100 mL, more preferably greater than 1,000 sec/100 mL, still more preferably greater than 1,200 sec/100 mL, and even more preferably equal to or greater than 1,500 sec/100 mL, and is preferably equal to or less than 10,000 sec/100 mL, more preferably equal to or less than 8,000 sec/100 mL, still more preferably equal to or less than 5,000 sec/100 mL, and even more preferably equal to or less than 4,000 sec/100 mL.

<21> The heating tool according to any one of <18> to <20>, in which on the premise that the degree of air permeability of the second bag sheet is preferably higher than the degree of air permeability of the first bag sheet, the degree of air permeability of the second bag sheet is preferably equal to or greater than 5,000 sec/100 mL, and more preferably equal to or greater than 8,000 sec/100 mL, and is more preferably equal to or less than 150,000 sec/100 mL, and more preferably equal to or less than 100,000 sec/100 mL.

<22> The heating tool according to any one of <18> to <21>, in which the steam generator is preferably accommodated so that the water absorbent sheet is on the side of the first bag sheet.

<23> The heating tool according to any one of <1> to <22>, in which the bag is preferably accommodated in the exterior body having the air permeability.

EXAMPLE

Example 1

A heating tool having the structure shown in FIG. 3 was prepared as follows.

[Preparation of Aqueous Dispersion of Heat Generation Powders]

The oxidizable metal, the carbon component, water, the reaction accelerator, the pH control agent, the thickener, and the like were prepared in the blending ratio (mass ratio) shown in the blending of Table 1 and the aqueous dispersion of heat generation powders (heat generation composition) was prepared by the following procedure. The thickener was dissolved in water, and thereafter the reaction accelerator and pH control agent were dissolved to prepare an aqueous solution. On the other hand, a powder premixed with an oxidizable metal and a carbon component was prepared, and a premixed powder was placed in an aqueous solution and stirred with a disk turbine type agitating blade at 150 rpm for 10 minutes to obtain a slurry-like aqueous dispersion of heat generation powders.

The types, product names and manufacturers of the oxidizable metal, the carbon component, water, the reaction accelerator, and the thickener are as follows.

Oxidizable metal: Iron powder (iron powder RKH, manufactured by Dowa IP CREATION Co., Ltd.) average particle diameter 45 μm Carbon component: Activated carbon (Carboraffin, manufactured by Japan EnviroChemicals Co., Ltd.) average particle diameter 40 μm Thickener: Xanthan gum (Echogum BT, manufactured by DSP Gokyo Food & Chemical Co., Ltd.) molecular weight 2,000,000

Water: Tap water pH control agent 1: Tripotassium phosphate (manufactured by Yoneyama Chemical Industry Co., Ltd.)

pH control agent 2: 48% potassium hydroxide solution (manufactured by Kanto Chemical Co., Ltd.)

Reaction accelerator: sodium chloride (Japanese Pharmacopoeia sodium chloride, manufactured by Tomita Pharmaceutical Co., Ltd.)

TABLE 1

| Composition | Blending ratio [%] |
| --- | --- |
| Iron powder | 55.2 |
| Water | 34.3 |
| Activated carbon | 4.4 |
| Xanthan gum | 0.1 |
| Tripotassium phosphate | 1.0 |
| Potassium hydroxide | 0.1 |
| Sodium chloride | 4.9 |
| Total | 100 |

[Preparation of Steam Generator]

Using a PE-laminated paper (manufactured by Nittoku Co., Ltd.) as a base material layer, an aqueous dispersion of heat generation powders was coated on the front surface of the base material layer of 24.01 $cm^2$ (4.9 cm×4.9 cm) with a thickness of approximately 3 mm. The aqueous dispersion of heat generation powders used at this time was 1.4 g.

Subsequently, 0.12 g of the water absorbent polymer (spherical, average particle diameter 300 μm, Aqualic CAW-151, manufactured by Nippon Shokubai Co., Ltd.) was sprayed on the coated surface of the above aqueous dispersion of heat generation powders with a thickness of approximately 0.5 mm (basis weight 50 $g/m^2$).

Subsequently, using a crepe paper (basis weight 63 $g/m^2$, manufactured by Daishowa Paper Industries Co., Ltd.) of 4.9 cm×4.9 cm as the water absorbent sheet, the steam generator was prepared by laminating and integrating on the sprayed portion of the water absorbent polymer.

The maximum water absorbing capacity of the water absorbent sheet used herein was measured by the method described below (the same hereinafter) to be 0.24 $g/cm^2$.

[Preparation of Heating Tool]

The steam generators obtained above were respectively put in the bag bodies having the air permeability (6.5 cm×6.5 cm: degree of air permeability of first bag sheet 1500 sec/100 ml, and second bag sheet is non-air permeable) so that the water absorbent sheet was on the side of the first bag sheet and the base material layer was on the side of the second bag sheet, and the peripheral edge portions were hermetically sealed.

Furthermore, in an outer packaging bag (7.5 cm×7.5 cm) made of an air-through nonwoven fabric (degree of air permeability 1 sec/100 mL, 30 $g/m^2$), the outer packaging bag coated with an adhesive compound on the peripheral surface of one side with a width of 1 cm×a length of 4 cm, 100 $g/m^2$, and covered with a release paper was prepared. The one in which the steam generator is accommodated in the bag was put in the outer packaging bag, and hermetically sealed the peripheral edge portion was used as a heating tool. The heating tool was put in an oxygen blocking bag until evaluation to be described later was performed. A series of work was performed under nitrogen stream.

Examples 2 to 6

Heating tools were prepared in the same manner as in Example 1, except that the maximum water absorbing capacity and the content of the water absorbent polymer of the used water absorbent sheet were as shown in Table 2 or 3.

Comparative Examples 1 to 3

Heating tools were prepared in the same manner as in Example 1, except that the maximum water absorbing capacity and the content of the water absorbent polymer of the used water absorbent sheet were as shown in Table 2 or 3.

[Evaluation]

Analysis and evaluation were performed on the steam generators of the above Examples and Comparative examples and the heating tools provided with the steam generators in the following points. The results are shown in Table 2 or Table 3.

1. Measurement of Moisture Content

The maximum water absorbing capacity and the moisture content of the water absorbent sheet and the moisture content of the heat generating layer, regarding the steam generator of the above Examples and Comparative examples were measured as follows.

<1> Measurement Method of Maximum Water Absorbing Capacity ($Z_{max}$) of Water Absorbent Sheet Only the water absorbent sheet was peeled off from the steam generator, washed with ion exchanged water, and dried by heating at 80° C. for 10 minutes. The water absorbent sheet after drying was cut to a size of approximately 5 cm square, and after measuring the area (S) [cm²] and the mass ($W_0$) [g], the water absorbent sheet was immersed in a 5% by mass sodium chloride aqueous solution for 5 minutes. The sheet was taken out with tweezers, and was hung and left in air for 5 minute to drip and drop moisture that could not be held. Thereafter, the mass ($W_1$) [g] was measured, and the maximum water absorbing capacity ($Z_{max}$) [g/cm²] of the water absorbent sheet was calculated from the following Formula (1).

$$Z_{max}=(W_1-W_0)/S \quad \text{(Formula 1)}$$

<2> Moisture Content ($W_{11}$) of Water Absorbent Sheet

Only the water absorbent sheet was peeled off from the steam generator, and the area (S) [cm²] and the mass ($W_2$) were measured. The mass of the water absorbent sheet after heating and drying at 80° C. for 10 minutes was measured ($W_3$), and the moisture content ($W_{11}$) of the water absorbent sheet was calculated with basis weight (g/m²) from the following Formula (2).

$$W_{11}=(W_2-W_3)/(S\times10^{-4}) \quad \text{(Formula 2)}$$

<3> Moisture Content ($W_{12}$) of Heat Generating Layer

Approximately 1 g of the heat generating layer formed on the base material was sampled and precisely weighed ($W_4$). The mass of the dried heat generating layer after heating and drying at 150° C. for 10 minutes was measured ($W_5$), and the moisture content of the heat generating layer was calculated from the following Formula (3).

$$W_{12}=(W_4-W_5)/W_4\times100 \quad \text{(Formula 3)}$$

2. Measurement of Heat Generation

By using a measuring instrument in accordance with JIS S4100, the side of the first bag sheet of the heating tool was attached to the measurement surface and a measurement of heat generation was performed. In this measurement of heat generation, the time axis is plotted as a horizontal axis and the temperature as a vertical axis.

In addition, [maximum temperature (° C.)], [temperature rising time (min)], and [duration time (min)] are obtained from the plot result. Specifically, [maximum temperature (° C.)] was taken as the highest temperature (° C.) between the start of measurement and the end of measurement, [temperature rising time (min)] as the time (minutes) required to reach from 35° C. to 45° C. from the start of measurement, and [duration time (min)] as the time (minutes) that was equal to or higher than 45° C. from the start of measurement to the end of measurement.

3. Steam Generation Amount

Figure 4:
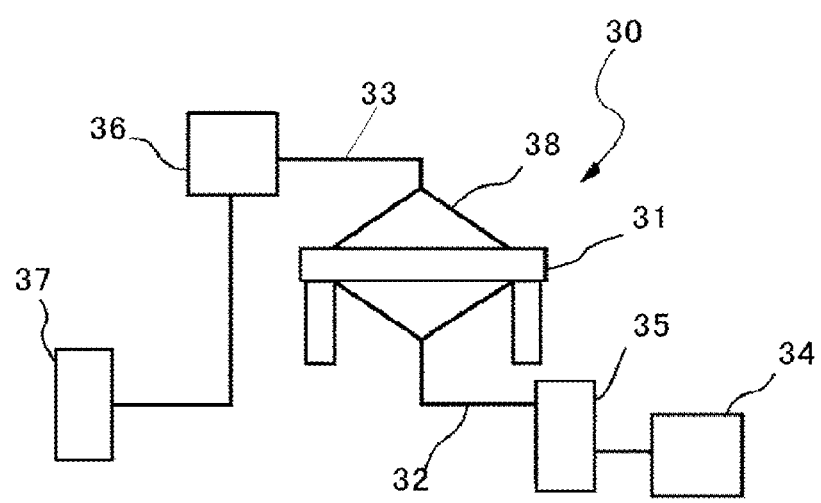
FIG. 4 is a schematic diagram showing an apparatus which measures the steam generation amount.

The steam generation amount is measured using a measuring apparatus 30 of the steam generation amount shown in FIG. 4 as follows. The measuring apparatus 30 of the steam generation amount shown in FIG. 4 is provided with an aluminum measurement chamber 31 (volume 2.1 L), an inflow path 32 through which dehumidified air (humidity less than 2% and flow rate 2.1 L/min) flows into the lower portion of the measurement chamber 31, and an outflow path 33 through which air flows out from the upper portion of the measurement chamber 31. An inlet thermo-hygrometer 34 and an inlet flow meter 35 are attached to the inflow path 32. On the other hand, an outlet thermo-hygrometer 36 and an outlet flow meter 37 are attached to the outflow path 33. A thermometer (thermistor) 38 is attached to the measurement chamber 31. As the thermometer 38, one having a temperature resolution of approximately 0.01° C. is used.

The heating tool is taken out from the packaging material, and placed on the measurement chamber 31 with the steam generation surface facing upward, at measurement environment temperature 30° C. (30±1° C.). The thermometer 38 with metal ball (4.5 g) attached was placed thereon. In this state, dehumidified air flowed from the lower portion of the measurement chamber 31. A difference between the absolute humidity before and after the air flows into the measurement chamber 31 was obtained from the temperature and the humidity measured by the inlet thermo-hygrometer 34 and the outlet thermo-hygrometer 36. Furthermore, the amount of steam discharged by the heating tool was calculated from the flow rate measured by the inlet flow meter 35 and the outlet flow meter 37. The steam generation amount for 10 minutes from the start of the measurement is shown in Table 2 or 3.

4. Skin Maximum Temperature

The heating tool obtained as described above was applied to the eyes and the skin temperature of the upper eyelid was measured using a temperature logger LT8A (manufactured by Gram Corporation). The highest temperature at 15 minutes of wearing was taken as the skin maximum temperature.

In Table 2 or Table 3, the highest temperature among the skin temperatures measured in this manner is shown as [skin maximum temperature [° C.]].

TABLE 2

| | | | Example | | | |
|---|---|---|---|---|---|---|
| | | | 1 | 2 | 3 | 4 |
| Coating amount of aqueous dispersion of heat generation powders when preparing steam generator | | g/cell | 1.4 | 1.4 | 1.4 | 1.4 |
| | | g/m² | 583 | 583 | 583 | 583 |
| Composition of steam generator | Content of water absorbent polymer in heat generating layer (basic weight) | g/m² | 50 | 40 | 30 | 50 |
| | Maximum water absorbing capacity of water absorbent sheet | g/cm² | 0.24 | 0.24 | 0.24 | 2.74 |
| | Basic weight of water absorbent sheet | g/m² | 63 | 63 | 63 | 388 |
| | Water absorbent sheet/ water absorbent polymer | mass ratio | 1.26 | 1.58 | 2.10 | 7.76 |
| | Degree of air permeability of bag sheet (TSF) | sec/100 ml | 1500 | 1500 | 1500 | 1500 |

TABLE 2-continued

| | | | | | | |
|---|---|---|---|---|---|---|
| | Activated carbon/iron powder | mass ratio | 8.0 | 8.0 | 8.0 | 8.0 |
| | Water absorbent polymer/iron powder | mass ratio | 15.5 | 12.4 | 9.3 | 15.5 |
| Evaluation | Maximum temperature | °C. | 61.6 | 62.9 | 59.2 | 61.4 |
| | Temperature rising time | min. | 1.4 | 1.4 | 1.8 | 1.3 |
| | Duration time | min. | 18.3 | 18.3 | 20.0 | 19.7 |
| | Steam generation amount (per cell) | mg/10 min · cell | 125.6 | 125.8 | 112.9 | 125.7 |
| | Steam generation amount (Per 1 g) | mg/10 min · g | 89.7 | 89.9 | 80.7 | 89.8 |
| | Steam generation amount (per 1 cm²) | mg/min · cm² | 5.23 | 5.24 | 4.70 | 5.23 |
| | Skin maximum temperature | °C. | 41.0 | 41.0 | 40.3 | 40.3 |

| | | | Example | | Comparative Example | | |
|---|---|---|---|---|---|---|---|
| | | | 5 | 6 | 1 | 2 | 3 |
| Coating amount of aqueous dispersion of heat generation powders when preparing steam generator | | | 1.4<br>583 | 1.4<br>583 | 1.4<br>583 | 1.4<br>583 | 1.4<br>583 |
| Composition of steam generator | Content of water absorbent polymer in heat generating layer (basic weight) | | 40 | 30 | 50 | 40 | 30 |
| | Maximum water absorbing capacity of water absorbent sheet | | 2.74 | 2.74 | 0.79 | 0.79 | 0.79 |
| | Basic weight of water absorbent sheet | | 388 | 388 | 24 | 24 | 24 |
| | Water absorbent sheet/water absorbent polymer | | 9.70 | 12.93 | 0.48 | 0.60 | 0.80 |
| | Degree of air permeability of bag sheet (TSF) | | 1500 | 1500 | 1500 | 1500 | 1500 |
| | Activated carbon/iron powder | | 8.0 | 8.0 | 8.0 | 8.0 | 8.0 |
| | Water absorbent polymer/iron powder | | 12.4 | 9.3 | 15.5 | 12.4 | 9.3 |
| Evaluation | Maximum temperature | | 59.9 | 61.1 | 62.5 | 63.4 | 62.8 |
| | Temperature rising time | | 1.3 | 1.3 | 1.5 | 1.5 | 2.0 |
| | Duration time | | 18.7 | 18.9 | 19.2 | 19.7 | 19.0 |
| | Steam generation amount (per cell) | | 97.7 | 105.4 | 140.7 | 133.1 | 112.2 |
| | Steam generation amount (Per 1 g) | | 69.8 | 75.3 | 100.5 | 95.1 | 80.1 |
| | Steam generation amount (per 1 cm²) | | 4.07 | 4.39 | 5.86 | 5.54 | 4.57 |
| | Skin maximum temperature | | 39.9 | 39.9 | 42.6 | 43.1 | 43.6 |

TABLE 3

| | | | Example | | | Comparative Example | |
|---|---|---|---|---|---|---|---|
| | | | 2 | 4 | 6 | 1 | 3 |
| Coating amount of aqueous dispersion of heat generation powders when preparing steam generator | | g/cell<br>g/m² | 1.4<br>583 | 1.4<br>583 | 1.4<br>583 | 1.4<br>583 | 1.4<br>583 |
| Composition of steam generator | Content of water absorbent polymer in heat cgenerating layer (basic weight) | g/m² | 40 | 50 | 30 | 50 | 30 |
| | Maximum water absorbing capacity of water absorbent sheet | g/cm² | 0.24 | 2.74 | 2.74 | 0.79 | 0.79 |
| | Basic weight of water absorbent sheet | g/m² | 63 | 388 | 388 | 24 | 24 |
| | Water absorbent sheet/water absorbent polymer | mass ratio | 1.58 | 7.76 | 12.93 | 0.48 | 0.80 |
| | Amount of water carried in water absorbent sheet | g/m² | 30.0 | 93.3 | 121.5 | 27 2 | 22.5 |
| | Degree of air permeability of bag sheet (TSF) | sec/100 ml | 1500 | 1500 | 1500 | 1500 | 1500 |
| | Activated carbon/iron powder | mass ratio | 8.0 | 8.0 | 8.0 | 8.0 | 8.0 |
| | Water absorbent polymer/iron powder | mass ratio | 12.4 | 15.5 | 9.3 | 15.5 | 9.3 |
| | Moisture content in heat generating layer | % by mass | 26.9 | 19.0 | 17.3 | 28.7 | 30.5 |

TABLE 3-continued

|  |  |  | Example | | | Comparative Example | |
| --- | --- | --- | --- | --- | --- | --- | --- |
|  |  |  | 2 | 4 | 6 | 1 | 3 |
| Evaluation | Maximum temperature | ° C. | 62.9 | 61.4 | 61.1 | 62.5 | 62.8 |
|  | Temperature rising time | min. | 1.4 | 1.3 | 1.3 | 1.5 | 2.0 |
|  | Duration time | min. | 18.3 | 19.7 | 18.9 | 19.2 | 19.0 |
|  | Steam generation amount (per cell) | mg/10 min · cell | 125.8 | 125.7 | 105.4 | 140.7 | 112.2 |
|  | Steam generation amount (Per 1 g) | mg/10 min · g | 89.9 | 89.3 | 75.3 | 100.5 | 80.1 |
|  | Steam generation amount (per 1 cm$^2$) | mg/min · cm$^2$ | 5.24 | 5.23 | 4.39 | 5.86 | 4.67 |
|  | Skin maximum temperature | ° C. | 41.0 | 40.3 | 39.9 | 42.6 | 43.6 |

As shown in Tables 2 and 3, the heating tools obtained in Examples were heating tools whose temperature rises faster than the heating tools obtained in each Comparative Example, and were excellent as the steam generation amount. In addition, the temperature of heat generation is appropriate, and in a case of being applied to the skin, it was the heating tool that can impart a comfortable warming feeling.

This application claims priority based on Japanese Patent Application No. 2015-144450 filed on Jul. 21, 2015 and Japanese Patent Application No. 2016-128749 filed on Jun. 29, 2016, the entire disclosure thereof is incorporated herein.

The invention claimed is:

1. A heating tool comprising:
   a steam generator having a heat generating layer which comprises an oxidizable metal, a carbon component, a water absorbent polymer, and water, laminated with a water absorbent sheet which carries water; and
   a bag at least a portion of which has an air permeability and which accommodates the steam generator,
   wherein the oxidizable metal and the carbon component are in contact with the water absorbent polymer, and
   wherein a mass ratio of the water absorbent sheet is 0.9 to 15 with respect to the water absorbent polymer contained in the heat generating layer.

2. The heating tool according to claim 1, wherein the amount of water carried in the water absorbent sheet is 28 g/m$^2$ to 150 g/m$^2$ in terms of basis weight.

3. The heating tool according to claim 1, wherein a content of water in the heat generating layer is 12% by mass to 28% by mass.

4. The heating tool according to claim 1, wherein a content of the water absorbent polymer in the heat generating layer is 5 parts by mass to 20 parts by mass with respect to 100 parts by mass of a content of the oxidizable metal.

5. The heating tool according to claim 1, wherein a mass proportion of the content of the water absorbent polymer to a content of the carbon component (water absorbent polymer/carbon component) in the heat generating layer is 0.4 to 5.

6. The heating tool according to claim 1, wherein at least a portion of the water absorbent polymer is disposed so as to be in contact with the water absorbent sheet.

7. The heating tool according to claim 1, wherein the water absorbent sheet is positioned on a skin side of the heating tool adapted to contact skin of a user, and the heat generating layer is disposed on a side of the heating tool opposite to the skin side of the heating tool.

8. The heating tool according to claim 1, wherein the basis weight of the water absorbent polymer contained in the heat generating layer is 25 g/m$^2$ to 80 g/m$^2$ in a dry state, and the basis weight of the water absorbent sheet is 100 g/m$^2$ to 400 g/m$^2$ in a dry state.

9. The heating tool according to claim 1, wherein the content of the carbon component is 0.3 parts by mass to 20 parts by mass with respect to 100 parts by mass of the content of the oxidizable metal.

10. The heating tool according to claim 1, wherein the heat generating layer further comprises a thickener.

11. The heating tool according to claim 10, wherein a content of the thickener is 0.05 parts by mass to 5 parts by mass with respect to 100 parts by mass of the oxidizable metal.

12. The heating tool according to claim 1, wherein the bag accommodating the steam generator comprises an air permeable sheet having a degree of air permeability of greater than 500 sec/100 mL and equal to or less than 10,000 sec/100 mL.

13. The heating tool according to claim 1, wherein a maximum water absorbing capacity of the water absorbent sheet is 0.1 g/cm$^2$ to 5 g/cm$^2$.

14. The heating tool according to claim 1, wherein the content of the oxidizable metal in the heat generating layer is 100 g/m$^2$ to 3,000 g/m$^2$ in terms of basis weight.

15. The heating tool according to claim 1, wherein a mass proportion of the content of the water to a content of the carbon component (water/carbon component) in the heat generating layer is 0.5 to 8.3.

16. The heating tool according to claim 1, wherein the mass ratio of the water absorbent sheet is 1.5 to 13 with respect to the water absorbent polymer contained in the heat generating layer.

17. The heating tool according to claim 1,
   wherein the bag accommodating the steam generator is configured to comprise a first bag sheet and a second bag sheet, and the first bag sheet and the second bag sheet are bonded to each other in an extension region extending outward from the periphery of the steam generator, and
   wherein the degree of air permeability of the second bag sheet is higher than the degree of air permeability of the first bag sheet, and is 5,000 sec/100 mL to 150,000 sec/100 mL.

18. The heating tool according to claim 17, wherein the steam generator is accommodated so that the water absorbent sheet is on the side of the first bag sheet.

19. The heating tool according to claim 1, wherein the water absorbent polymer is not in the water absorbent sheet.

20. A heating tool comprising:
   a steam generator having a heat generating layer which contains an oxidizable metal, a carbon component, a water absorbent polymer, and water, laminated with a water absorbent sheet which carries water; and a bag at least a portion of which has an air permeability and which accommodates the steam generator, wherein the oxidizable metal and the carbon component are in contact with the water absorbent polymer, and wherein a basis weight of the water absorbent polymer contained in the heat generating layer is 20 $g/m^2$ to 100 $g/m^2$ in a dry state, and a basis weight of the water absorbent sheet is 50 $g/m^2$ to 500 $g/m^2$ in a dry state.

21. The heating tool according to claim 20, wherein no part of the water absorbent polymer is in the water absorbent sheet.

* * * * *